(12) United States Patent
Azimpoor et al.

(10) Patent No.: US 9,226,732 B2
(45) Date of Patent: Jan. 5, 2016

(54) BONE MARROW ASPIRATION DEVICE AND NEEDLE

(75) Inventors: Ali Faghani Azimpoor, Houston, TX (US); Lou Blasetti, Quincy, MA (US); Mark Kibbe, Carver, MA (US); Russell Hart, Taunton, MA (US)

(73) Assignee: HARVEST TECHNOLOGIES CORPORATION, Lakewood, CO (US)

( * ) Notice: Subject to any disclaimer, the term of this patent is extended or adjusted under 35 U.S.C. 154(b) by 880 days.

(21) Appl. No.: 13/303,345

(22) Filed: Nov. 23, 2011

(65) Prior Publication Data
US 2013/0131545 A1 May 23, 2013

(51) Int. Cl.
*A61B 10/02* (2006.01)
*A61B 19/00* (2006.01)

(52) U.S. Cl.
CPC ....... *A61B 10/025* (2013.01); *A61B 2010/0258* (2013.01); *A61B 2019/304* (2013.01); *Y10T 29/49826* (2015.01)

(58) Field of Classification Search
CPC .......... A61B 5/150175; A61B 10/205; A61B 10/025; A61B 2019/304; A61B 2010/0258
USPC ............... 604/117, 158–159, 164.01–164.04, 604/164.09–164.11, 165.01–165.04, 604/166.01, 171, 181, 562–572
See application file for complete search history.

(56) References Cited

U.S. PATENT DOCUMENTS

| | | | |
|---|---|---|---|
| 3,598,108 A | 8/1971 | Jamshidi | |
| 3,628,524 A | 12/1971 | Jamshidi | |
| 4,258,722 A | 3/1981 | Sessions et al. | |
| 4,314,565 A | 2/1982 | Lee | |
| 4,469,109 A | 9/1984 | Mehl | |
| 4,486,188 A | 12/1984 | Altshuler et al. | |
| 5,257,632 A | 11/1993 | Turkel et al. | |
| 5,320,608 A * | 6/1994 | Gerrone | 604/117 |
| 5,368,046 A | 11/1994 | Scarfone et al. | |
| 6,730,071 B1 | 5/2004 | Dassa | |
| 6,846,314 B2 | 1/2005 | Shapira | |

(Continued)

FOREIGN PATENT DOCUMENTS

| | | |
|---|---|---|
| CA | 1183751 | 3/1985 |
| CN | 201353163 | 12/2009 |

OTHER PUBLICATIONS

Written Opinion and International Search Report Dated Apr. 1, 2013 for PCT/US2012/066275.

(Continued)

*Primary Examiner* — Theodore Stigell
*Assistant Examiner* — Amber Stiles
(74) *Attorney, Agent, or Firm* — Heslin Rothenberg Farley & Mesiti P.C.

(57) ABSTRACT

Devices for extracting bone marrow from a bone of a patient are disclosed. The device includes a housing defined in part by a cannula and a hollow needle disposed within the cannula. The hollow needle is movable axially relative to the cannula and extendable therefrom. The hollow needle is configured to aspirate bone marrow within a bone. A depth adjustment mechanism coupled to the hollow needle and the cannula is used to adjust the depth of the hollow needle relative to the cannula to control the distance of the needle within the bone. The device is attachable to an extraction device to extract bone marrow from the patient through the hollow needle. Methods of using these devices and methods of extracting bone marrow are also included.

24 Claims, 4 Drawing Sheets

(56) References Cited

U.S. PATENT DOCUMENTS

| | | |
|---|---|---|
| 7,015,038 B2 | 3/2006 | Chang et al. |
| 7,637,872 B1 | 12/2009 | Fox |
| 2004/0127814 A1 | 7/2004 | Negroni |
| 2004/0153005 A1* | 8/2004 | Krueger ........................ 600/571 |
| 2006/0276747 A1* | 12/2006 | Moos et al. ................... 604/117 |
| 2008/0015503 A1* | 1/2008 | Jansen et al. ................. 604/117 |
| 2009/0054808 A1 | 2/2009 | Miller |
| 2011/0082425 A1 | 4/2011 | Wuestemann et al. |
| 2011/0082441 A1* | 4/2011 | Allee et al. .................... 604/506 |
| 2012/0226301 A1* | 9/2012 | Geist .............................. 606/172 |

OTHER PUBLICATIONS

European Search Report for corresponding European Application 12850950.2, mailed on Apr. 24, 2015.

* cited by examiner

BONE MARROW ASPIRATION DEVICE AND NEEDLE

BACKGROUND OF THE INVENTION

1. Technical Field

The present invention generally relates to devices and methods for extracting tissue such as bone marrow from a patient. More particularly, the present invention relates to bone marrow aspiration needle and device.

2. Background Information

U.S. Pat. Nos. 3,628,524 and 3,598,108 disclose a device that is commonly used for tissue biopsy. In general, such devices include a cannula, in which a stylet is inserted and used to penetrate the outer layers of tissue. Once the outer layers of tissue have been penetrated, a needle is advanced to the desired depth. Then the stylet is removed and a syringe is attached to the proximal end and tissue is extracted via the needle.

Limitations exist with prior art including controlling the needle penetration depth in bone, visualization of the bone entry location and rotational movement of the cannula that could affect tissue. For example, the presence of a T-shaped handle, flange or other member that is used to brace the device may block the surgeon's view of the device in the patient thus making it more difficult to maneuver the device. Also, such devices do not include a needle, the depth of which within the patient may be adequately adjusted, relative to the cannula to accommodate the anatomy of a patient. Furthermore, rotational movement of the cannula and needle when inserted can result in damage to surrounding bone or other tissue as the needle is inserted or extracted.

These issues make it difficult to safely extract bone marrow from certain anatomical areas such as vertebrae. Bone marrow and/or concentrated bone marrow products are used in spinal fusion surgery to facilitate bone growth and healing. In such surgeries, the surgeon may prefer to extract the bone marrow from vertebrae at or near the point of surgery, rather than create a new surgical site. When extracting bone marrow from the vertebrae, conventional bone marrow extraction/aspiration needles are difficult to use and control, especially when using an anterior surgical approach. For example, if the cannula or needle rotates, tissue may be exposed to possible injury due to the needle and the cannula. In addition, due to the vertebrae anatomical limitations as compared to the ileum and the surrounding anatomy, it is desirable to have an access needle which is variable and adjustable in length so its depth within the bone can be precisely controlled.

Thus, a need exists for an adjustable depth bone marrow aspiration device that is safe, effective and able to accommodate a diverse array of clinical scenarios, including spinal surgery and/or vertebral bone marrow extraction.

SUMMARY OF THE INVENTION

The present invention provides a safe and effective adjustable depth bone marrow aspiration device through the incorporation of several innovative design characteristics enabling the device to be safely and easily used in a variety of applications.

The present invention provides, in a first aspect, a bone marrow aspiration device for extracting bone marrow from a bone of a patient including a housing defined in part by a cannula which functions as an elongate hollow guide for an access needle. A hollow access needle is co-axially disposed within the cannula, and movable axially relative thereto and being extendable therefrom. The needle is non-rotatable relative to the cannula. The needle is configured to access bone marrow within a bone of a patient. The needle also receives a stylet, which is co-axially inserted therein and used to puncture bone. A depth adjustment mechanism is operatively connected to the needle and the cannula to adjust the axial position of the needle relative to the cannula. The depth of the needle into the bone of the patient is controlled by the depth adjustment mechanism. One or more stop guards are coupled to the needle and/or the housing to prevent detachment of the needle and the housing. The housing is attachable to an extraction device to extract bone marrow from the patient through the needle. The needle and the cannula do not rotate relative to each other and relative to the bone during depth adjustment of the needle, including into the bone of the patient.

The present invention provides, in a second aspect, a method of manufacturing a bone marrow aspiration device for collecting bone marrow from a patient. The method includes providing a housing defined in part by a cannula. A hollow needle is disposed within the cannula and is movable axially relative thereto and extendable therefrom. A depth adjustment mechanism is operatively engaged with the needle and the cannula to adjust the axial position of the needle relative to the cannula. One or more stop guards are used to prevent detachment of the needle and housing. The housing is attachable to an extraction device to extract bone marrow from the patient through the needle. The needle and the cannula do not rotate relative to each other or the bone during depth adjustment of the needle.

In another aspect, the invention provides a method of aspirating bone marrow from a patient. The method includes the steps of penetrating the bone of a patient with the aforementioned device such that the needle is in communication with the bone marrow then extracting the bone marrow using the device, and collecting the bone marrow in a collection means.

These and other objects, features and advantages of this invention will become apparent from the following detailed description of the various aspects of the invention taken in conjunction with the accompanying drawings.

DETAILED DESCRIPTION OF THE INVENTION

In this detailed description and claims, the words proximal and/or distal are defined by their standard usage for indicating a particular disposition of a surgical instrument or component thereof. For example, "proximal" means the portion of the instrument or subcomponent that is positioned nearest the patient, while "distal" indicates the part of the instrument farthest from the patient.

In a first aspect, the present invention includes a device for extracting bone marrow from within bone of a patient. The device includes a cylindrical housing defined in part by a cannula. A hollow needle is co-axially disposed within the cannula. The hollow needle is non-rotatable relative to the cannula, but movable axially relative thereto and extendable therefrom. The needle is configured to access and aspirate bone marrow within the bone of a patient. The needle receives a stylet, which is co-axially inserted therein and used to penetrate and puncture bone. A depth adjustment mechanism is operatively connected to the needle and the cannula to adjust the axial position of the needle relative to the cannula. The depth of the needle into the bone of the patient is controlled by the depth adjustment mechanism. One or more stop guards are attached to the needle and/or the housing to prevent detachment of the hollow needle and the housing. The housing is attachable to an extraction device such as a syringe to aspirate bone marrow from the patient through the hollow needle. The needle and the cannula do not rotate relative to each other and relative to the bone during depth adjustment of the needle.

Figure 1:
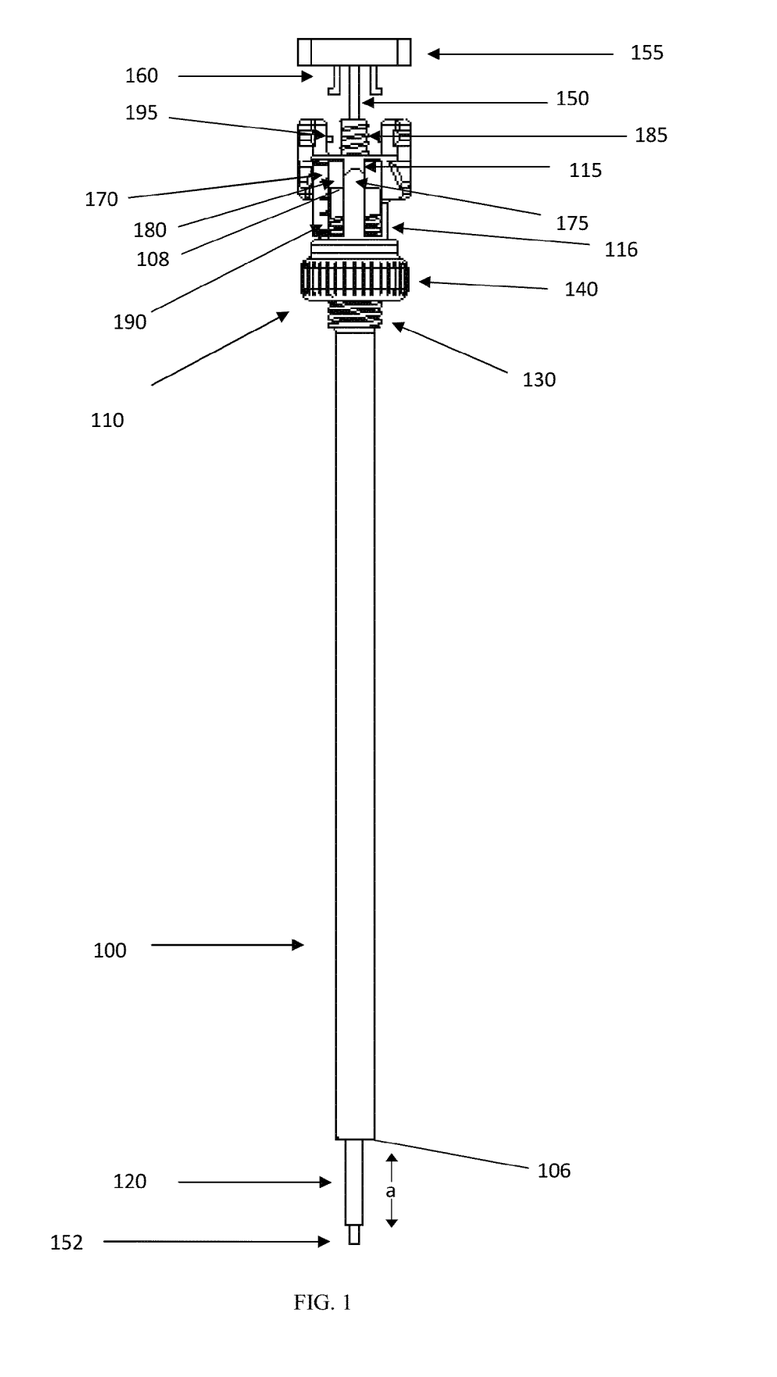
FIG. 1 depicts a front view of the bone marrow aspiration device of the present invention.

As shown in FIG. 1, a bone marrow aspiration needle including a housing defined in part by a hollow guide or cannula (100) is shown. The cannula (100) is cylindrical and elongate in shape to allow the device to penetrate deep into the body. Co-axially inserted within the cannula (100) is a hollow needle (120). The exposed tip or end of the needle (120) protrudes from the end of the cannula (100) at its end a particular exposed distance "a". The opposite end (175) of the needle (120) is affixed to the opposite end of the device proximate the depth adjustment mechanism (110). The exposed distance "a", is adjustable so that the exposed tip (152) of the needle relative to the cannula (100) may be adjusted using the depth adjustment mechanism (110).

The needle (120) is configured to allow for the aspiration of bone marrow therethrough from the exposed end to the opposite end proximate the depth adjustment mechanism (110). Also, the needle is configured to allow for the insertion of a stylet coaxially (150) therethrough. The stylet has a tip which is configured to puncture cortical bone. The cannula can be made of varying lengths and diameters to accommodate many clinical scenarios including vertebral bone marrow extraction, each of which may require different needle types. The needle (120) typically contains openings at or near its tip (152) (not shown) through which to extract tissue.

During insertion of the device into the patient, the stylet (150), being inserted into the cannula penetrates bone, such as the vertebrae. After penetration of the vertebrae is achieved, the stylet (150) is removed and the hollow needle (120) is then used to aspirate a portion of the marrow. The stylet (150) has a handle (155) or other protrusion such that the stylet (150) may be easily gripped for insertion or removal into or out of the hollow needle (120). The stylet is constructed to sustain the forces necessary to penetrate bone. Typically, a mallet is used to impact against the top of the stylet (155) to drive the stylet through the cortical bone.

Figure 3:
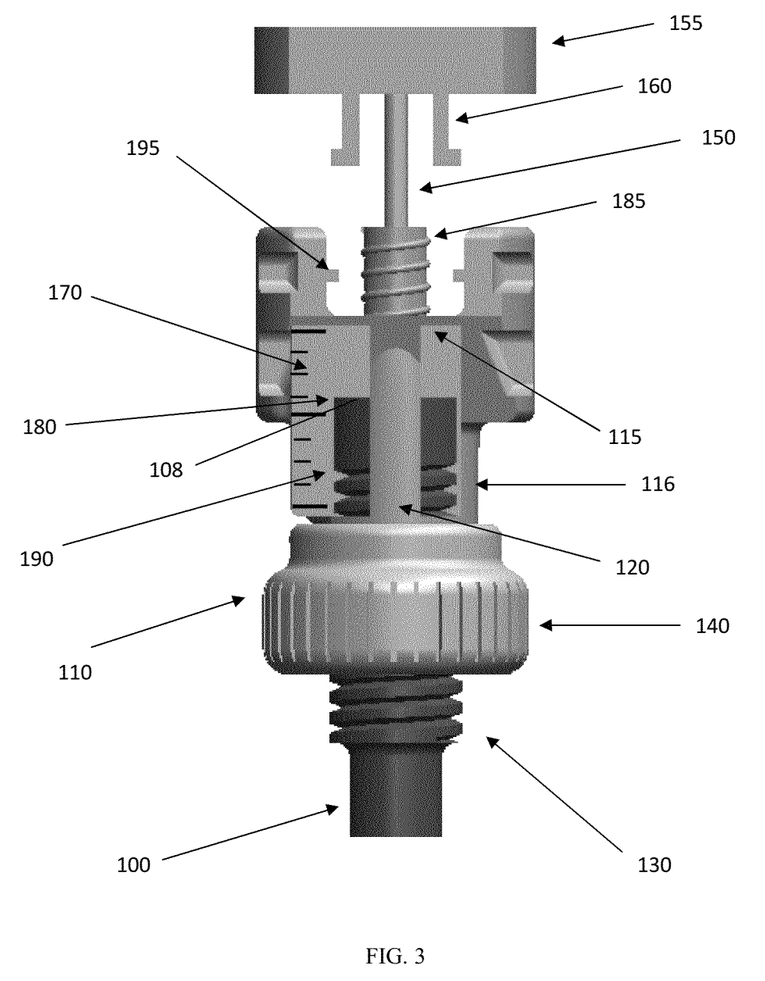
FIG. 3 shows an exploded view of the depth adjustment mechanism of the device according to one aspect of the invention and surrounding components.

Shown in FIG. 1 is an exemplary stylet design. Specifically, the stylet (150), as shown in FIG. 3, includes a top portion (155) into which two arms (160) are constructed that may be used to secure the stylet in place. In one aspect of the invention shown in FIG. 3, the depth adjustment mechanism (110) includes two stops (195) on the distal end of the depth adjustment mechanism (110). The stops (195) are in the form of ridges or tabs which extend from the housing handle (116) radially inward within a cavity. The arms (160) are received within the cavity when the stylet is fully inserted. The top (155) of the stylet may be rotated to allow the arms to avoid the stops (195). Then the stylet may be rotated such that the arms (160) are locked underneath the mechanical stops (195), thus securing the stylet (150) into the device. Alternative mechanisms of securing the stylet into the device are within the scope of the invention. Such mechanisms may include: a threaded mechanism, use of a locking pin, as well as any other application-appropriate mechanism that would secure the stylet in place during insertion into the patient.

Figure 2:
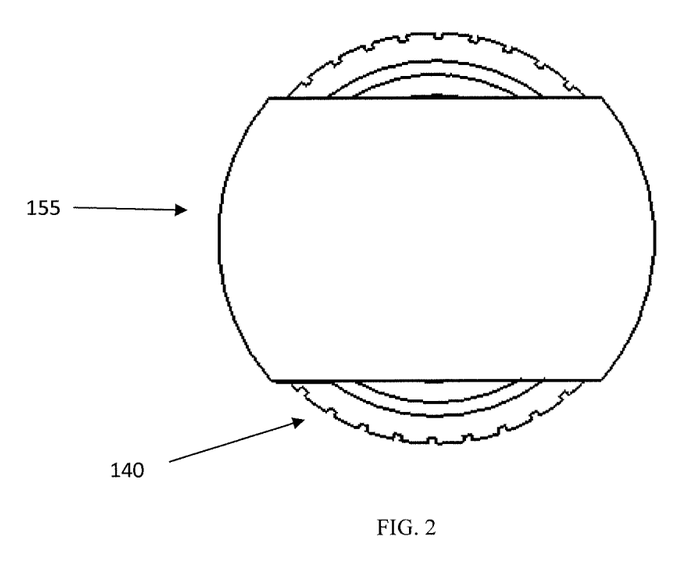
FIG. 2 depicts a top view of the device of FIG. 1.

The aspiration device of the present invention maximizes the surgeon's view of the device into the patient. FIG. 2 shows a top-down view of the bone marrow aspiration device which has a minimal vertical profile. The stylet, with a top handle (155) the depth adjustment thumbwheel (140), are shown. The aspiration device is of cylindrical form which allows the surgeon a substantially unobstructed view of the device and needle at the point of insertion into the patient. As shown in FIG. 2, the top of the stylet (155) when viewed in the axial direction from a distal view occupies a relatively small projection or surface area. The width of the stylet top (155), handle (116) and thumbwheel (116) are only slightly larger than the diameter of the cannula (100). For example, the width of such parts should be two times or less larger than the diameter of the cannula. Due to the length of the device, via the relatively small size of the handle (155) allows the surgeon to view the proximal portions of the device, the axial direction, when inserted into the patient without substantial obstruction of such a view. In typical prior art aspiration needles, a handle occupies substantially larger area so as to effectively obstruct the surgeon's view of the proximal end of the device making such devices impractical for use in anterior surgical procedures including the spinal fusion procedures where aspiration of bone marrow is desired.

The depth adjustment mechanism (110) functions to move the needle (120) located within the cannula (100) axially relative thereto to adjust the exposed distance "a" of the hollow needle (120), thus increasing or decreasing the length of the device. The depth adjustment mechanism (110) may take several forms including a threaded mechanism, a pneumatic mechanism, a hydraulic mechanism, an electrically-driven mechanism, a dialing mechanism, or another application-appropriate mechanism. One exemplary aspect of the invention is found in FIG. 1 wherein the depth adjustment mechanism (110) includes a thumbwheel (140) operatively engaged to the housing handle (116). The thumbwheel (140) is rotatable relative to the handle (116). The distal end of the hollow needle (120) is affixed to the handle (116) so that the needle (120) does not move relative to the handle (116). The cannula (100) engages the thumbwheel (140) by the threads (130) and the hollow needle (120) is mounted directly to the inside of the cannula, terminating within the handle (116). The thumbwheel (140) has internal threads and rotation of the thumbwheel (140) moves the cannula (100) in the axial direction increasing or decreasing distance "a" as the wheel travels proximately or distally along the threads (130) present on the cannula (100). The thumbwheel is able to rotate relative to the cannula (100) and handle (116), but is not axially moveable relative to the handle (116).

The depth adjustment mechanism (110) may be calibrated to allow for a range of exposed needle lengths ("a"). For example, if the invention is being used for vertebral marrow extraction the depth adjustment mechanism (110) may be calibrated such that the possible range of exposed needle lengths is between 5 and 30 millimeters and preferably between 10 and 27 millimeters. Medical imaging techniques, such as x-ray devices may be used to monitor the depth of penetration of the needle into the bone.

The depth adjustment mechanism (110), in certain embodiments, may also include a depth indicator (170). In FIGS. 1 and 3, the depth indicator (170) is a visual scale showing the approximate length of the exposed needle. Other configurations of the depth indicator are described in the context of FIG. 3. When the depth of the needle is adjusted the needle (120) does not rotate relative to the cannula (100).

Rather, the needle and cannula translate relative to each other in the axial direction above. Eliminating such rotation, helps avoid tissue becoming caught between the cannula (100) and needle (120).

There may be one or more stops built into the depth adjustment mechanism (110) to prevent the device from detaching during use. These stops can be placed on one or more of the cannula (100), hollow needle (120), depth adjustment mechanism (110) and/or handle (116). In FIGS. 1 and 3, there are two mechanical stops shown. The first stop includes a block (180) in the form of a surface within the handle (116) such that when the depth adjustment mechanism (110) is adjusted for maximum needle (120) exposure, the block (180) contacts the top (108) of the cannula (100), preventing further movement of the cannula (100). The second mechanical stop (190) includes a termination of the threads (130) on the cannula (100) such that when the thumbwheel (140) is adjusted to the second mechanical stop (190), it is prevented from further rotation. These mechanical stops prevent the depth adjustment mechanism from allowing for needle exposure lengths "a" (not shown) beyond a particular range and also prevents the invention from disassembling, including potentially the needle or cannula detaching from the device and injuring the patient.

The device also includes a means for connecting the aspiration device to an extraction device. As shown in FIG. 1 the connection means (185) may be located on the distal end of the handle (116) and may also accommodate insertion of a stylet (150) or other application-appropriate item. Examples of connection means (185) within the scope of the invention include, but are not limited to, Luer lock connections, Luer slip connections, and the like.

FIG. 3 depicts an exploded view of the depth adjustment mechanism (110) along with an indicator (170) to allow a user to determine the length of the exposed needle. The indicator (170) may be a visual indicator. The indicator (170) includes a number of depth markings in, for example, millimeters. A corresponding line of other means may be located on the cannula (not shown). The movement of the line on the guide relative to the indicator markings represents the change in depth of the needle. The indicator (170) may also be a tactile or audio indicator. An example of an audio indicator is found in FIG. 4. The audio indicator may be in the form of a series of tabs (400) affixed to the exterior surface of the cannula (100) that move axially as the depth of exposed needle (not shown) is adjusted and a series of strips (410) present on the interior surface of the depth adjustment mechanism (110) such that, as the amount of exposed needle (not shown) is adjusted, the tabs are driven axially across the strips, resulting in a "click" type sound, indicating a specific amount of adjustment, for example, one millimeter.

Penetration of the bone may be accomplished using any technique known in the art for accomplishing such a task, including inserting a stylet in the hollow needle and using a blunt force by from, for example, a mallet to drive the tip of the stylet through the bone of interest. Once such penetration is accomplished, the stylet may be removed and the hollow needle used as described elsewhere herein.

Examples of surgical procedures wherein the invention is useful is in the removal and collection of vertebral bone marrow for use during anterior spinal fusion, posterior lumbar fusion, lateral lumbar fusion, thoracic spinal fusion, and/or cervical fusion. However, use of the device with respect to an anterior lumbar spinal fusion surgery wherein the patient is lying on his or her back will now be described. According to known techniques, an incision is made in the patient's skin, to allow for anterior access. The device is then inserted into the patient by inserting proximal portion of the cannula (100) into the patient through the incision. The stylet tip (152) and exposed portion of the hollow needle (120) are manipulated by the surgeon within the patient to avoid tissue damage within the body. The device is continuously manipulated until the depth of the stylet (152) contacts the vertebrae. Thereafter, the bone marrow aspiration device is used to penetrate the vertebrae. The stylet maintains the structural integrity and fluid pathway of the needle during insertion. By striking the top handle of the stylet (155) with a mallet, the stylet tip (152) is forced through the vertebral cortical bone and into the vertebral bone marrow. When the stylet punctures the bone, the end (106) of the cannula contacts the outer bone surface of the patient such that distance "a" of the needle (120) penetrates the bone.

Figure 4:
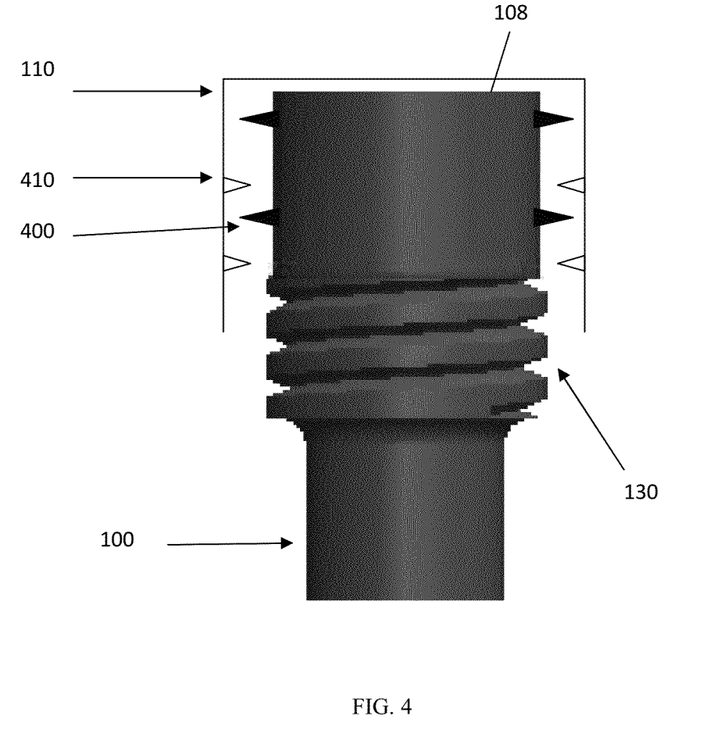
FIG. 4 illustrates an exploded view of an exemplary audio or tactile indicator mechanism useable with the aspiration device of the invention.

Once penetration of the vertebral bone marrow is achieved, the stylet is removed. The amount of exposed needle is adjusted to provide for a desired depth of penetration. The depth of the needle within the bone marrow is defined by contact of the cannula end (106) with the outer cortical bone of the vertebrae. An imaging device, typically, for example, an x-ray imaging device, is used by the surgeon to view and monitor the depth of penetration, i.e. distance "a" of the hollow needle. By rotating the thumbwheel of the depth adjustment mechanism, the distance of the needle "a" may be adjusted to the desired distance by the surgeon. Preferably, the depth adjustment mechanism is capable of adjusting the depth in increments of one millimeter or less. By viewing the calibrations on the depth adjustment mechanism, the surgeon can move the needle, for example, in one millimeter increments in order to obtain the desired distance within the vertebrae. In addition, as shown in FIG. 4, an audio and/or tactile indicator of movement of the needle in a defined increment may be used by the surgeon. By viewing the depth of the needle within the vertebrae via the x-ray device and adjusting the needle specific distances using the depth adjustment mechanism, the surgeon can precisely control the distance of the needle within the vertebrae.

Next, aspiration of the patient's bone marrow is accomplished. For example, a syringe (not shown) is attached to the device embodied in FIG. 1, via flexible tubing and a Luer lock attachment, which connects to Luer connection (185). Once the syringe is properly attached, extraction of the bone marrow occurs through use of the syringe to aspirate the bone marrow out of the vertebrae, through the needle (120) and into the body of the syringe itself. Once the bone marrow has been collected within the body of the syringe, any necessary step to achieve desired processing or storage conditions may be used. In some situations, it will be desired to accumulate significant amounts of bone marrow using this technique and then to concentrate the bone marrow for injection back into the patient, such as in a spinal fusion scenario. In a spinal fusion procedure, concentrated vertebral bone marrow is injected into the surgical site to enhance healing and fusion of the subject vertebrae.

Extraction of bone marrow using aspects of the invention may be accomplished in a variety of ways. Alternative methods of extracting bone marrow include the use of vacuum forces or mechanical means for generating extractive force, for example, negative pressure. A variety of devices are capable of generating appropriate extractive force including pumps, syringes, and other devices and all such devices are contemplated as within the scope of this aspect of the invention.

With respect to collecting the marrow, a range of collection means may be used. Such means can range from a simple syringe tube, to a collection bag, to any other application-appropriate collection means or systems. The collections means may be attached to the devices of the present invention in any application-appropriate manner, including through use of a Luer lock or Luer slip connection. The collection means may include features that perform functions distinct from collection such as filtration, concentration, and testing. For example, a collection system disclosed in co-pending U.S. patent application Ser. No. 13/303,407 entitled "System for Collecting and Processing Bone Marrow" by Azimpoor et al. filed on the same day as this application, and incorporated by reference herein in its entirety, may be used to collect and process the aspirated bone marrow.

Aspects of the invention are attachable to one or more bone marrow extraction devices. In the context of the present invention the term "extraction device" means a device capable of creating sufficient negative pressure, or another condition, for drawing bone marrow out of a bone via the hollow needle described in the context of aspects of the invention. Examples of such extraction means include, but are not limited to, a syringe or a vacuum pump. The extraction means may be attached to the devices of the present invention in any application-appropriate manner including through use of a Luer lock or. Luer slip connection, including, for example, through a Luer-lock connection with a port built into the housing of the device.

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention.

The invention claimed is:

1. A bone marrow aspiration device for extracting marrow from a bone of a patient, comprising:
   a housing defined in part by a cannula, wherein the cannula includes threads on an exterior surface and positioned near a distal end and a stop member positioned at a proximal end of said cannula;
   a hollow needle disposed within said cannula so as to be movable axially relative to said cannula and extendable therefrom, said hollow needle being non-rotatable relative to said cannula and being configured to receive a stylet coaxially inserted therein to penetrate bone to access bone marrow within said bone of said patient;
   a depth adjustment mechanism coupled to said hollow needle and said cannula to adjust an axial position of said hollow needle relative to said cannula, wherein a depth of said needle into said bone of said patient is controlled by said depth adjustment mechanism, the depth adjustment mechanism comprising:
   a thumbwheel mounted on said distal end of said cannula and including threads on an interior surface, the threads of the thumbwheel configured to mate with the threads on the cannula;
   one or more stop guards coupled to one or more of said hollow needle, said housing, and said depth adjustment mechanism to prevent detachment between said hollow needle and said housing or limit the axial position of said hollow needle relative to said cannula;
   said housing being attachable to an extraction device to extract bone marrow from said patient through said hollow needle;
   wherein said hollow needle and said cannula do not rotate relative to each other and relative to said bone during depth adjustment of said needle into said bone.

2. The device of claim 1, wherein the stylet includes a handle, said housing and said handle being sized and configured, relative to said cannula, to allow an unobstructed view of the entry point of the needle into the patient when viewed from a distal axial direction.

3. The device of claim 1, wherein the depth adjustment mechanism allows for a needle exposure length of between about 5 millimeters and about 30 millimeters.

4. The device of claim 1, wherein the device further comprises a depth indicator.

5. The device of claim 1, wherein the extraction device is a port.

6. The device of claim 1, wherein the device further comprises a collection means.

7. The device of claim 6, wherein the collection means is a bag or a tube.

8. The device of claim 1, wherein the depth adjustment mechanism is a wheel.

9. A method of manufacturing a bone marrow aspiration device for collecting bone marrow from a patient, the method comprising:
   providing a housing defined in part by a cannula with threads on an exterior surface and positioned near a distal end and a stop member positioned at a proximal end of said cannula;
   providing a hollow needle disposed within said cannula so as to be movable axially relative to said cannula and extendable therefrom, said hollow needle being non-rotatable relative to said cannula;
   operatively engaging a depth adjustment mechanism positioned at the distal end of the cannula, the depth adjustment mechanism with interior threads to said hollow needle and said cannula to adjust an axial position of said hollow needle relative to said cannula by coupling the interior threads of the depth adjustment mechanism to the threads of the cannula;
   providing one or more mechanical stop guards to one or more of said hollow needle, said housing, and said depth adjustment mechanism to prevent detachment between said hollow needle and said housing or limit the axial position of said hollow needle relative to said cannula;
   wherein said housing is attachable to an extraction device to extract bone marrow from said patient through said hollow needle, wherein said hollow needle and said cannula do not rotate relative to each other and relative to said bone during depth adjustment of said needle into said bone.

10. The method of claim 9, wherein a stylet includes a handle, said housing and said handle being sized and configured, relative to said cannula, to allow an unobstructed view of the entry point of the needle into the patient when viewed from a distal axial direction.

11. The method of claim 9, wherein the depth adjustment mechanism allows for a needle exposure length of between about 5 millimeters and about 30 millimeters.

12. The method of claim 9, wherein the device further comprises a depth indicator.

13. The method of claim 9, wherein the extraction device is a port.

14. The method of claim 9, wherein the device further comprises a collection means.

15. The method of claim 14, wherein the collection means is a bag or a tube.

16. The method of claim 9, wherein the depth adjustment mechanism is a wheel.

17. A method of aspirating bone marrow from a patient comprising:
   making an incision in the patient to expose a site for aspiration;

obtaining a bone marrow aspiration device comprising:
- a housing defined in part by an elongate hollow guide with exterior threads positioned near a distal end and a stop member positioned at a proximal end of said elongate hollow guide;
- a hollow needle disposed within said hollow guide and moveable axially relative to said hollow guide to be extendable therefrom, said hollow needle being configured to receive a stylet coaxially inserted therein;
- a depth adjustment mechanism coupled to said hollow needle and said hollow guide at the distal end, wherein the depth adjustment mechanism includes internal threads; and
- one or more mechanical stop guards coupled to one or more of said hollow needle, said housing, and said depth adjustment mechanism;
- said housing being attachable to an extraction device;
- wherein said exterior threads of the hollow guide rotatably couple to the internal threads of the depth adjustment mechanism; inserting the hollow guide into the patient through the incision;

positioning said hollow needle and said stylet to engage said stylet with a bone of said patient, said hollow needle being non-rotatable relative to said hollow guide;

penetrating said bone with said stylet and said hollow needle to access bone marrow within said bone of said patient;

removing said stylet from said bone;

adjusting an axial position of said hollow needle relative to said hollow guide, wherein a depth of said needle into said bone of said patient is controlled by said depth adjustment mechanism, said hollow needle and said hollow guide do not rotate relative to each other or relative to said bone during depth adjustment of said needle into said bone, and said one or more mechanical stop guards preventing detachment between said hollow needle and said housing or limiting the axial position of said hollow needle relative to said hollow guide during adjustment of said axial position of said hollow needle; and extracting said bone marrow from said patient through said hollow needle.

18. The method of claim 17, wherein the stylet includes a handle, said housing and said handle being sized and configured, relative to said hollow guide, to allow an unobstructed view of the entry point of the needle into the patient when viewed from a distal axial direction.

19. The method of claim 17, wherein the depth adjustment mechanism of the device allows for a needle exposure length of between about 5 millimeters and about 30 millimeters.

20. The method of claim 17, wherein the device further comprises a depth indicator.

21. The method of claim 17, wherein the extraction device is a port.

22. The method of claim 17, wherein the device further comprises a collection means.

23. The method of claim 22, wherein the collection means is a bag or a tube.

24. The method of claim 17, wherein the depth adjustment mechanism is a wheel.

* * * * *